United States Patent [19]
Chen

[11] Patent Number: 5,587,061
[45] Date of Patent: Dec. 24, 1996

[54] DEVICE AND METHOD FOR BIOMOLECULE PURIFICATION

[76] Inventor: Stephen L. Chen, 1300 SW. 185th Ave., Aloha, Oreg. 97007

[21] Appl. No.: 563,445

[22] Filed: Nov. 28, 1995

[51] Int. Cl.[6] .......................... G01N 27/26; G01N 27/447
[52] U.S. Cl. .......................... 204/613; 204/456; 204/462; 204/465; 204/606; 204/615
[58] Field of Search .................................. 204/615, 613, 204/606, 465, 462, 456

[56] References Cited

U.S. PATENT DOCUMENTS

| | | | |
|---|---|---|---|
| 3,533,933 | 10/1970 | Strauch | 204/615 |
| 3,539,493 | 11/1970 | Dorman | 204/615 |
| 3,579,433 | 5/1971 | Dahlgren | 204/615 |
| 3,616,454 | 10/1971 | Levy et al. | 204/615 |
| 3,697,406 | 10/1972 | Svendsen | 204/613 |
| 3,822,197 | 7/1974 | Nees et al. | 204/613 |
| 3,914,168 | 10/1975 | Allington | 204/606 X |
| 3,956,099 | 5/1976 | Israel et al. | 204/615 |
| 3,980,546 | 9/1976 | Caccavo | 204/615 |
| 4,111,785 | 9/1978 | Roskam | 204/615 |
| 4,479,861 | 10/1984 | Hediger | 204/615 |
| 4,877,510 | 10/1989 | Chen | 204/613 |
| 5,151,165 | 9/1992 | Huynh | 204/615 |
| 5,284,559 | 2/1994 | Lim et al. | 204/461 |

OTHER PUBLICATIONS

Pharmacia Biotech Inc. 1995 Products Catalog pp. 325–326.
* No month available.

Primary Examiner—Bruce F. Bell
Assistant Examiner—John S. Starsiak, Jr.

[57] ABSTRACT

A novel device and method for biomolecule purification is provided as a handy tool for routine applications when both a high resolution and an easy manipulation are required. A sample is applied into a device and the different biomolecules are separated from each other and stored in segregated liquid fractions in the device automatically after 1 hour electrophoresis. These purified biomolecules in liquid fractions are then easily released from the device in 4 minutes.

6 Claims, 1 Drawing Sheet

DEVICE AND METHOD FOR BIOMOLECULE PURIFICATION

BACKGROUND OF THE INVENTION

1. Field of the Invention

The invention relates to devices and methods for biomolecule purification.

2. Description of the Prior Arts

Gel filtration chromatography and conventional preparative gel electrophoresis are two of the most popular means employed for biomolecule purifications.

In gel filtration chromatography, a buffer flows through a matrix in a column. A sample of biomolecule mixture applied over the matrix is carried across the matrix by the flow of the buffer. There are numerous pores existing on the beads of the matrix. The separation of biomolecules relies on movement of the biomolecules into and out of the pores. The biomolecules at sizes larger than that of the pores can not enter the pores and move rapidly across the matrix. The biomolecules at sizes smaller than that of the pores enter and leave the pores repeatedly and therefore retain longer in the matrix. A separation between a group of large biomolecules and a group of small ones is then achievable by collecting them into separated fractions.

In conventional preparative gel electrophoresis, buffer does not flow through a gel matrix. But all biomolecules have to travel across the pores of the gel matrix. Movement of biomolecules is driven by an interaction between a net charge of the biomolecules and an electric potential applied on the gel matrix. The migration rate of a given biomolecule in the gel matrix is determined by its size, its shape, its net charge, the pore size of the gel matrix, and the potential difference of the electric potential. Thus different biomolecules in a mixture can be distinctly separated from each other at high resolution by sequentially collecting eluted fractions from a preparative gel apparatus. The migration rate of biomolecules in conventional preparative gel electrophoresis is much slower than that in gel filtration chromatography so that an extended process of fraction collection is unavoidable during electrophoresis. Thus an external fraction collector is essentially required.

Gel filtration chromatography devices and methods gain their popularity in routine biomolecule purifications by their speed and convenience. Pharmacia Biotech Inc. describes, for example, a series of pre-packed disposable gel filtration columns in its catalog of 1995 as a handy tool for such applications. These devices and methods, however, fail to achieve further purification whenever a higher resolution is required.

Conventional preparative gel electrophoresis devices and methods are utilized for high demanding biomolecule purifications when high resolution is a critical issue. Dorman U.S. Pat. No. 3,539,493 teaches, for example, a device and method of conventional preparative gel electrophoresis. It requires an installation of a special ion-permeable glass disc 108, an external fraction collector connecting to a elution tubing 70, two external mechanical pumps connecting to buffer inlet 94 and port 88 respectively, and a complicated procedure of assembly and disassembly of the device for each application. Hediger U.S. Pat. No. 4,479,861 teaches a device and method of conventional preparative gel electrophoresis. It requires an installation of a dialysis membrane, an external fraction collector, two external mechanical pumps, and a complicated procedure of assembly and disassembly for each application as well. Caccavo U.S. Pat. No. 3,980,546 teaches a device and method of conventional preparative gel electrophoresis. An external fraction collector and two external mechanical pumps, while a dialysis membrane is omitted, are still required for its function. Huynh U.S. Pat. No. 5,151,165 teaches a device and method of conventional preparative gel electrophoresis. To omit the requirement of using external mechanical pump, a delicate installation of an elution chamber is introduced. Besides, an external fraction collector and a dialysis membrane are still unavoidable. Similar examples can also be found at Chen U.S. Pat. No. 4,877,510 and Lim et al U.S. Pat. No. 5,284,559. The advantage of high resolution of these devices and methods, however, exhibits no attraction in applications of routine biomolecule purifications due to their complicated setup procedure, their high labor tensity, their tedious cleanup process, and their requirements of using an external fraction collector, using external pumps, and using a large bench space. The feasibility of these devices and methods is even ended in applications in which the material to be purified is radioactive or is at an extremely low amount level.

None of existing devices and methods own both high resolution and convenience together simultaneously. But, there are numerous routine biomolecule purifications in which both high resolution and handy to use are highly desired.

SUMMARY OF THE INVENTION

It is, thereafter, an object of the invention to integrate a capacity of high resolution in gel electrophoresis and a characteristic of convenience in gel filtration chromatography together to form a handy tool for routine biomolecule purifications.

The advantages of the invention are:

A. Its resolution capacity is much higher than that of gel filtration chromatography devices and methods. Different biomolecules in a mixture can be separated from each other distinctly by employing a column of preparative gel electrophoresis.

B. Its manipulation procedure is fundamentally easier than that of conventional preparative gel electrophoresis devices and methods. A complex gel column installation is omitted. An elution chamber installation is omitted. An external pump installation is omitted. An external fraction collector installation is omitted. And finally all of unnecessary disassembly manipulations after application are omitted.

C. It converts a slow process of fraction collection during electrophoresis in conventional preparation gel electrophoresis into a rapid process of releasing stored fractions, which omits the requirement of using an external fraction collector.

D. Its integrated structure makes the cleanup procedure is much easier than that of conventional preparative gel electrophoresis devices and methods.

E. Its compact format exhibits great flexibility in purifications of radioactive materials in which the space behind a protection shield is limited.

F. It solves the problem of liquid evaporation in conventional preparative gel electrophoresis devices and methods by storing fractions in an internal tubing during electrophoresis.

DETAILED DESCRIPTION OF THE PREFERRED EMBODIMENT

Figure 1:
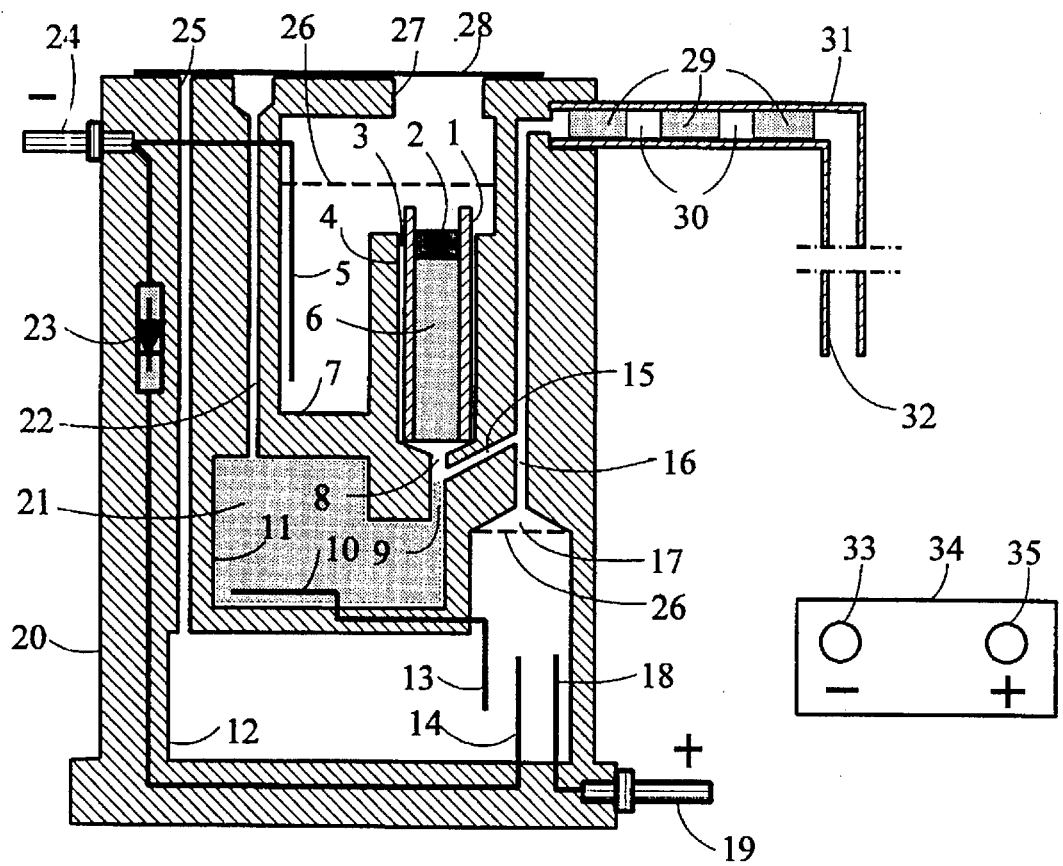
FIG. 1 is a cross-sectional view of a device according to the invention. It includes a gel column, a sealing tape, and a modified gel electrophoresis enclosure consisting of an integrated non-separable body, a silicon diode, a fraction storage tubing, and five electrodes.

FIG. 1 shows a cross-sectional view of a preferred embodiment of the invention.

A gel column 1, with a length of 3 cm and an interior diameter of 0.5 cm, contains a gel matrix 6 which is the same as those used in conventional gel electrophoresis. A sample 2 is introduced onto gel matrix 6. An interaction between an electric field and a net charge of the biomolecules in sample 2 drives the biomolecules to migrate downwards through gel matrix 6. Gel column 1 fits column channel 4 loosely so that a gap 3 between them serves as a path for a flow of a second buffer 26 from an upper chamber 7 to a buffer channel 8. The flow through second buffer 26 carries separated biomolecules away from the bottom of gel matrix 6 when these biomolecules migrate across gel matrix 6.

The operation procedure of the device and method is as follows:

A first buffer 21 is introduced into a lower chamber 11 to fullness via a balance channel 22.

A second buffer 26 in 140 ml volume is introduced into both an upper chamber 7 and an air chamber 12 via an inlet 27.

A gel column 1 is placed into column channel 4 via inlet 27.

A sample 2 is introduced into gel column 1.

A sealing tape 28 is finally placed on top side of an integrated non-separable body 20 to seal inlet 27, balance channel 22, and vent 25.

An electric potential is impressed to the device for an one hour electrophoresis by connecting a negative connector 24 to a negative outlet 33 and a positive connector 19 to a positive outlet 35 of a power supplier 34, and by setting power supplier 34 to a scale of 60 volts.

An electric potential is also impressed to the device, after electrophoresis, for releasing all fractions 29 from a fraction storage tubing 31 by inverting the connection of negative connector 24 to positive outlet 35 and positive connector 19 to negative outlet 33 of power supplier 34, and by maintaining the same voltage as that used for electrophoresis.

At end of the application, the device is easily cleared by removing sealing tape 28 and rinsing with water. Gel column 1 will come out during rinsing when turning the device upside down.

The mechanism of the device and method is as follows:

First buffer 21 and second buffer 26 have the same composition except that an additional 1M NaCl is added to first buffer 21. Second buffer 26 flows into air chamber 12 automatically via a buffer channel 8, a buffer channel 15, and an air channel 16 while it is being introduced into upper chamber 7. The air in air chamber 12 is released from vent 25 so that second buffer 26 flows into air chamber 12 smoothly. But basically, second buffer 26 can not flow into lower chamber 11. The diameter of balance channel 22 is only 1.5 mm. The surface level of first buffer 21 in lower chamber 11 therefore rises immediately in balance channel 22 when a negligible amount of second buffer 26 flows in from buffer channel 9. Hence, a gravity balance between first buffer 21 and second buffer 26 enables first buffer 21 to blockade buffer channel 9.

During electrophoresis, air bubbles are generated from electrode 5, electrode 10, electrode 13, and electrode 18. Electrode 14 has no function while in electrophoresis stage because a silicon diode 23 blocks its electric current. The air pressure in sealed upper chamber 7, lower chamber 11, and air chamber 12 is increasing when more and more air bubbles are generated. In upper chamber 7, the increasing air pressure drives second buffer 26 to flow to buffer channel 8. In lower chamber 11, the increasing air pressure forces first buffer 21 to flow to buffer channel 9. The outflows of second buffer 26 and first buffer 21 are then mixed and squeezed into buffer channel 15. The increasing air pressure in air chamber 12, in contrast to the other two chambers, does not drive an outflow of second buffer 26 from air chamber 12. The air bubbles generated are collected in an air space 17 and released into air channel 16. A competition of fighting for their way to a fraction storage tubing 31 occurs between buffer outflow from buffer channel 15 and air outflow from air channel 16. The air pressure in air channel 16 is further increasing when the buffer outflow from buffer channel 15 to fraction storage tubing 31 blocks air channel 16. A turn over of path occupancy will be reached when the strength of air pressure in air channel 16 is greater than that of buffer outflow in buffer channel 15. The air outflow from air channel 16 now blocks buffer outflow from buffer channel 15 and finds its way to fraction storage tubing 31. The pressure in buffer channel 15 will be getting higher and higher during blockage. Eventually, the buffer outflow from buffer channel 15 will resume its occupancy to fraction storage tubing 31 and blocks the air outflow again. The stage of competition turns over periodically so that the buffer outflow is segregated into fractions 29 by air gaps 30 in fraction storage tubing 31.

The biomolecules carried in outflow of second buffer 26 have a tendency of migrating into buffer channel 9. But the outflow of first buffer 21 at an opposite direction in buffer channel 9 excludes these biomolecules and turns them to buffer channel 15. The inclusion of 1M NaCl in first buffer 21 secures the blockage. Different biomolecules in buffer outflow are then sequentially carried into different fractions in fraction storage tubing 31.

To release the fractions for further manipulation after electrophoresis, the connection between connectors and outlets is inverted. That is, switching positive connector 19 to negative outlet 33 and negative connector 24 to positive outlet 35 of power supplier 34. Air bubbles, when the connections are inverted and the same voltage is maintained, are generated acutely from electrode 14 and electrode 18 because silicon diode 23 now conducts a high electric current to electrode 14 and electrode 18. The fast moving air pushes all fractions 29 in fraction storage tubing 31 to move out from outlet 32. The time for releasing all fractions 29 is only 4 minutes and the manner of fraction releasing is at an evenly drop by drop pattern, which allow one to collect fractions 29 into a set of 1.5 ml microcentrifuge tubes easily without using an external fraction collector.

The circuit of electric current, during electrophoresis, is from positive connector 1, via electrode 18, second buffer 26 in air chamber 12, electrode 13, electrode 10, first buffer 21 in lower chamber 11, gel matrix 6, second buffer 26 in upper chamber 7, electrode 5, to negative connector 24. The level of electric current ranges about 5 mA when power supplier 34 is et to 60 volts. Silicon diode 23, however, short-circuits the pathway and elevates the current to about 80 mA under the same voltage while working at fraction releasing condition.

Other features of the preferred embodiment are as follows:

Air chamber 12 can hold buffer at volume of 100 ml. Electrodes 13, 14, and 18 are placed under air space 17. Electrode 14 and electrode 18 should be placed at a distance 2 cm apart from each other.

Lower chamber 11 is capable of containing 30 ml of buffer. Buffer channel 9 connects lower chamber 11 at a lower level in height and stays away from electrode 10 so that the accumulated air at top side of lower chamber 11 does not escape to buffer channel 9. An even level should be maintained among the top side of lower chamber 11, buffer channel 8, an buffer channel 15.

Upper chamber 7 has enough space for 50 ml of buffer. Inlet 27 has a diameter of 1 cm and is constructed right above column channel 4.

A piece of Teflon tubing with a length of 120 cm and an interior diameter of 0.4 cm is used as fraction storage tubing 31. The volume capacity of fraction storage tubing is 15 ml. To form a compact format and block radiation emission in applications with radioactive material, fraction storage tubing 31 is arranged in a spring-like shape and fixed inside an acrylic container.

For easy sealing, inlet 27, balance channel 22, and vent 25 are closely constructed on top side of integrated non-separable body 20. A clear acrylic material is used for constructing integrated non-separable body 20, which allows one to moniter the conditions in all chambers and channels clearly from outside.

A 1.5 mm diameter is designed for balance channel 21, buffer channel 8, buffer channel 9, buffer channel 15, and air channel 16. The length of buffer channel 8 is as short as 1 mm and the length of buffer channel 9 is 5 mm.

Silicon diode 32 is rated at 400 V of peak inverse voltage and 1A of forward current and is constructed inside integrated non-separable body 20.

Although the description above contains specifications, it will be apparent to those skilled in the art that a number of other variations and modifications may be made in this invention without departing from its spirit and scope. A cover, for example, can be used for sealing inlet 27, balance channel 21, and vent 25, the length and interior diameter of column 1 can be extended, the current circuit can be arranged in other patterns, the 1M NaCl in first buffer 21 can be omitted if one more electrode is placed in lower chamber 11, and first buffer 21 and second buffer 26 can be introduced into inlet 27 in a single step if the 1M NaCl is omitted. Thus, the description as set out above should not be constructed as limiting the scope of the invention but as merely providing illustration of one of the presently preferred embodiment of this invention.

What is claimed is:

1. A device of modified preparative gel electrophoresis for biomolecule purification, comprising a lower chamber containing a first buffer and electrode for conducting an electric field of electrophoresis, a balance channel, with a substantially reduced volume capacity, uprising from said lower chamber, said balance channel being sealable by a sealing means for trapping air bubbles generated within said lower chamber, an upper chamber containing a second buffer and an electrode for conducting said electric field of electrophoresis, an inlet on top side of said upper chamber, said inlet being sealable by said sealing means for trapping air bubbles generated within said upper chamber, an air chamber containing said second buffer and three electrodes immersed in said second buffer, a silicon diode in electric circuit having direct connection with one of said three electrodes in said air chamber for controlling electric current of said one of said three electrodes, a vent connected to said air chamber, said vent being sealable by said sealing means for trapping air bubbles generated within said air chamber, a column channel vertically connecting said upper chamber to said lower chamber via a buffer channel, said buffer channel, with a substantially reduced diameter, located between said column channel and said lower chamber and join to said lower chamber at a site immersed in said first buffer, said column channel located beneath said inlet with said upper chamber and immersed by said second buffer from said upper chamber, a gel column fitted in said column channel loosely for easy placement, gap between said gel column and said column channel being permeable for said second buffer from said upper chamber to said buffer channel, and a fraction storage tubing receiving an outflow of said first buffer from said lower chamber, an outflow of said second buffer from said upper chamber, and an outflow of said air bubbles from said air chamber via a channel means, said channel means linked to said buffer channel at the middle and joined to said air chamber on its top.

2. The device of claim 1 wherein said inlet, said balance channel, and said vent are located on top of said device.

3. The device of claim 1 wherein the volume capacity of said fraction storage tubing is 15 ml.

4. A method of modified preparative gel electrophoresis for biomolecule purification, comprising (a) providing a device having a lower chamber containing a first buffer and an electrode for conducting an electric field of electrophoresis, a balance channel, with a substantially reduced volume capacity, uprising from said lower chamber, said balance channel being sealable by a sealing means for trapping air bubbles generated within said lower chamber, an upper chamber containing a second buffer and an electrode for conducting said electric field of electrophoresis, an inlet on top side of said upper chamber, said inlet being sealable by said sealing means for trapping air bubbles generated within said upper chamber, an air chamber containing said second buffer and three electrodes immersed in said second buffer, a silicon diode in electric circuit having direct connection with one of said three electrodes in said air chamber for controlling electric current of said one of said three electrodes, a vent connected to said air chamber, said vent being sealable by said sealing means for trapping air bubbles generated within said air chamber, a column channel vertically connecting said upper chamber to said lower chamber via a buffer channel, said buffer channel, with a substantially reduced diameter, located between said column channel and said lower chamber and joined to said lower chamber at a site immersed in said first buffer, said column channel located beneath said inlet with said upper chamber and immersed by said second buffer from said upper chamber, a gel column fitted in said column channel loosely for easy placement, a gap between said gel column and said column channel being permeable for said second buffer from said upper chamber to said buffer channel, and a fraction storage tubing receiving an outflow of said first buffer from said lower chamber, an outflow of said second buffer from said upper chamber, and an outflow of said air bubbles from said air chamber via a channel means, said channel means linked to said buffer channel at the middle and joined to said air chamber on its top side, (b) introducing said first buffer into said lower chamber, (c) introducing said second buffer into said upper chamber and said air chamber, (d) placing said gel column into said column channel, (e) introducing a sample into said gel column, (f) sealing said inlet, said balance channel, and said vent with said sealing means, (g) impressing said electric field of electrophoresis to said device from a power supplier for electrophoresis of said sample, and (h) impressing said electric field of electrophoresis at an inverted polarity to said device from said power supplier for releasing said fractions from said fraction storage tubing.

5. The method of claim 4 wherein said first buffer contains NaCl at a concentration of 1M.

6. The method of claim 4 wherein said fractions are released from said fraction storage tubing into 1.5 ml microcentrifuge tubes in 4 minutes.

* * * * *